(12) United States Patent
Davis et al.

(10) Patent No.: US 10,722,378 B2
(45) Date of Patent: Jul. 28, 2020

(54) SURGICAL IMPLANT INCLUDING A BODY PORTION AND AT LEAST ONE ATTACHED TIER

(71) Applicant: Warsaw Orthopedic, Inc., Warsaw, IN (US)

(72) Inventors: Darren L. Davis, Arlington, TN (US); Eric C. Lange, Collierville, TN (US); Anthony J. Melkent, Germantown, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 115 days.

(21) Appl. No.: 16/107,694

(22) Filed: Aug. 21, 2018

(65) Prior Publication Data
US 2020/0060839 A1   Feb. 27, 2020

(51) Int. Cl.
*A61F 2/44*   (2006.01)
*A61F 2/30*   (2006.01)

(52) U.S. Cl.
CPC .......... *A61F 2/447* (2013.01); *A61F 2/30771* (2013.01); *A61F 2002/3082* (2013.01); *A61F 2002/3093* (2013.01); *A61F 2002/30153* (2013.01)

(58) Field of Classification Search
CPC ...... A61F 2/4455; A61F 2/446; A61F 2/4465; A61F 2/447; A61F 2/30771
See application file for complete search history.

(56) References Cited

U.S. PATENT DOCUMENTS

| 5,609,635 A | 3/1997 | Michelson |
| 2003/0191531 A1* | 10/2003 | Berry ................... A61F 2/4455 623/17.11 |
| 2011/0190888 A1* | 8/2011 | Bertele ............... A61F 2/30734 623/17.11 |
| 2014/0277491 A1 | 9/2014 | Fang et al. |

FOREIGN PATENT DOCUMENTS

| CN | 104706446 | 6/2015 |
| JP | 2017-006686 | 1/2017 |

OTHER PUBLICATIONS

International Search Report and Written Opinion dated Dec. 2, 2019 from International Application No. PCT/US2019/046440.

* cited by examiner

*Primary Examiner* — Si Ming Ku

(57) ABSTRACT

A surgical implant includes a body portion, a first tier, and a second tier. The first tier is attached to an upper surface of the body portion, and the second tier is attached to a lower surface of the body portion. Each of the upper surface and the lower surface of the body portion includes channels formed therein. The first tier includes a first layer including a plurality of first slats and a second layer including a plurality of second slats, where the plurality of first slats and the plurality of second slats intersect one another to form openings therebetween. The second tier includes a third layer including a plurality of third slats and a fourth layer including a plurality of fourth slats, where the plurality of third slats and the plurality of fourth slats intersect one another to form openings therebetween. When the first tier and the second tier are attached to the body portion, a passageway is formed through the openings formed in the first tier to the channels in the upper surface of the body portion, and a passageway is formed through the openings (Continued)

formed in the second tier to the channels in the lower surface of the body portion.

18 Claims, 9 Drawing Sheets

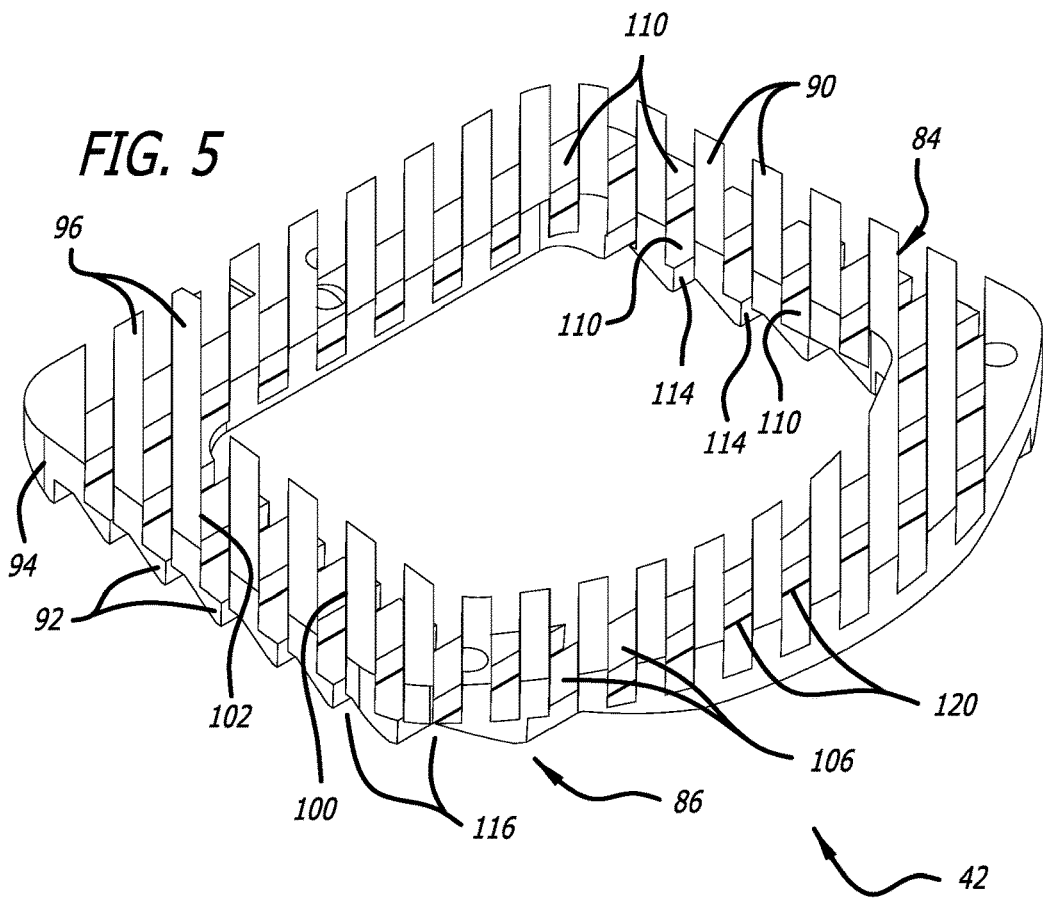
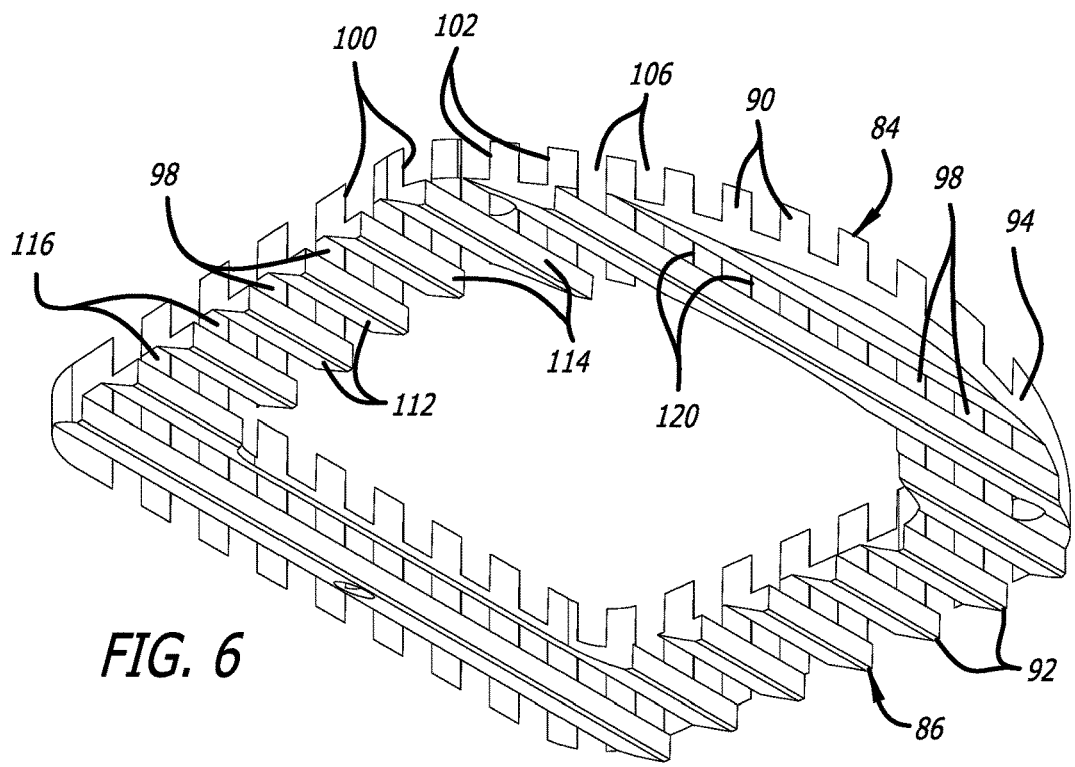

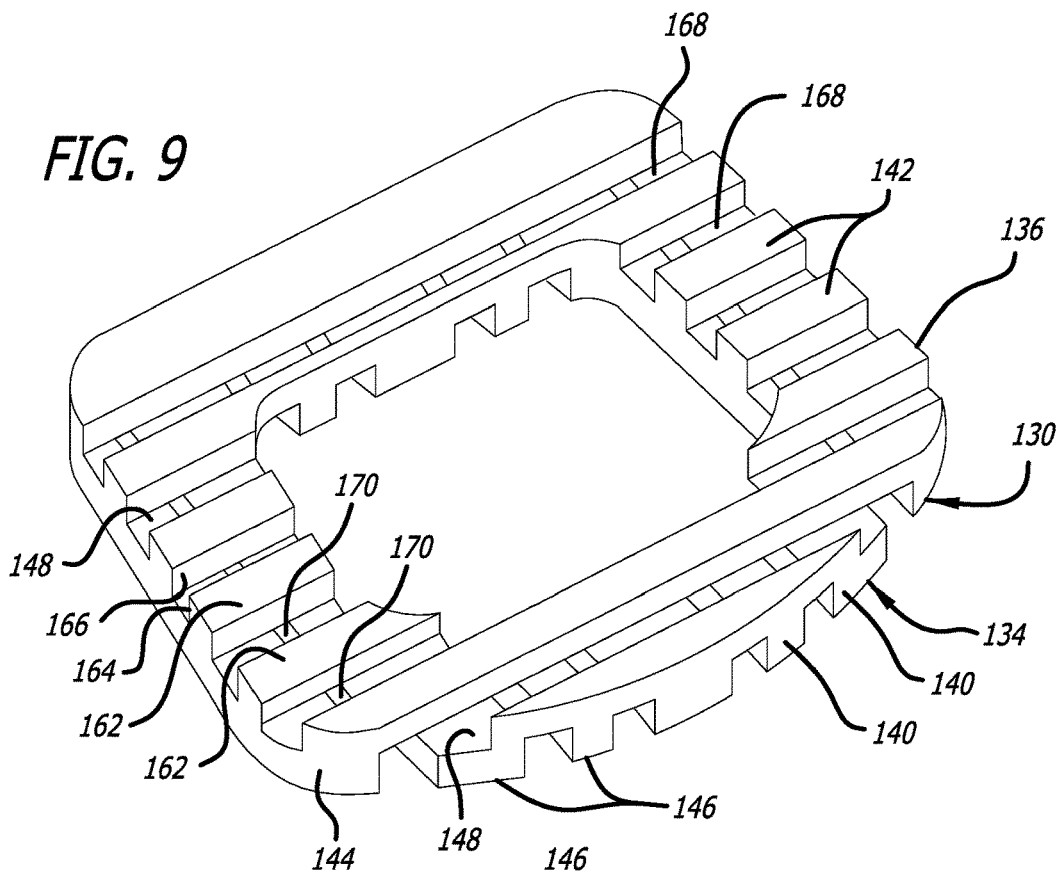
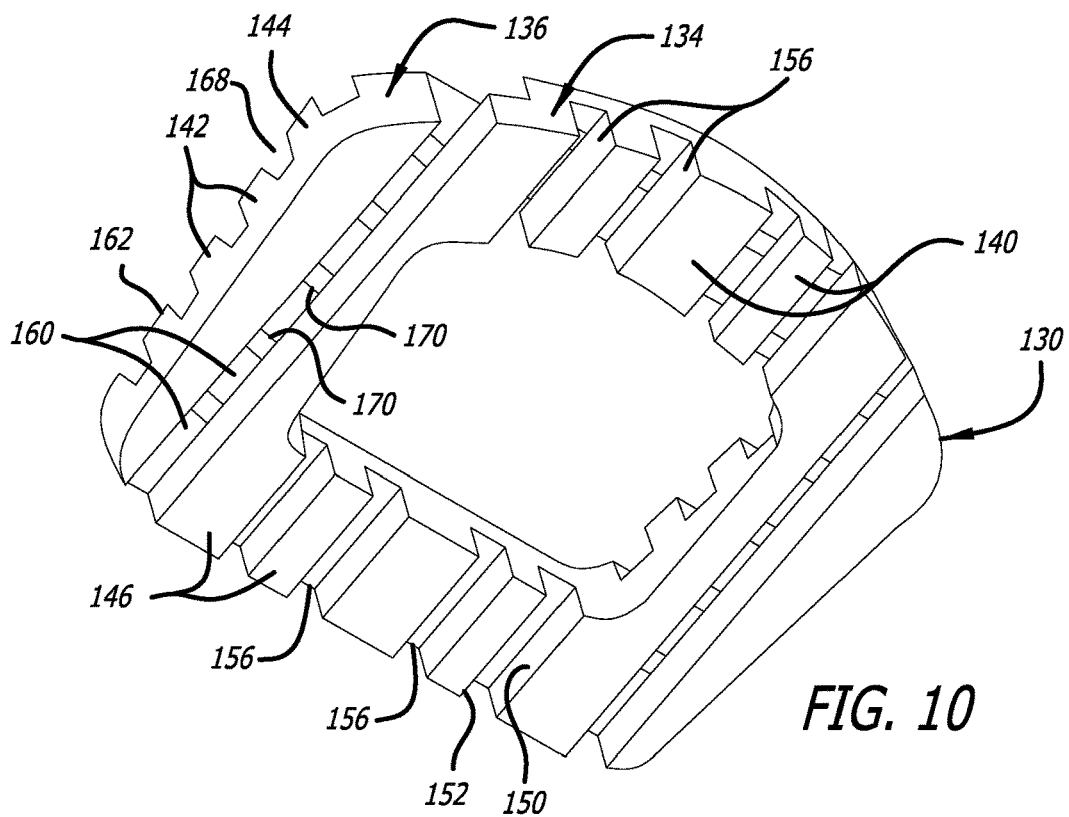

SURGICAL IMPLANT INCLUDING A BODY PORTION AND AT LEAST ONE ATTACHED TIER

FIELD

The present technology is generally related to a surgical implant having a body portion and at least one tier attached to one of an upper surface or a lower surface of the body portion, where the body portion includes channels formed in the one of the upper surface and the lower surface, and the at least one tier includes a first layer of slats forming first channels and a second layer of slats forming second channels.

BACKGROUND

Surgical implants have been used in the human body to aid repair of anatomical deficiencies such as a damaged vertebral columns and broken bones. Spinal implants for implantation into a disc space between adjacent vertebral bodies oftentimes include bone contacting surfaces having surface configurations that afford insertion and resist migration of the spinal implants in the disc space. For example, upper surfaces and lower surfaces of such spinal implants can be provided with ratchetings angled to both afford insertion and resist migration of the spinal implant in the disc space. Spinal implants for implantation into the disc space between the adjacent vertebral bodies also oftentimes include cavities formed therein that provide for bone ingrowth into and therethrough to facilitate fusion of the surgical implants to bone. For example, apertures can be formed through such implants to form pathways for facilitating bone ingrowth. However, processes for removing materials from a workpiece to have such surface configurations and pathways can be limiting and time consuming. To illustrate, machining processes are oftentimes constrained by the physical limitations involved with accessing portions of the workpiece and the time required for the machining processes. Therefore, there is a need for surgical implants that can be constructed of separate components that can provide for such surface configurations and/or pathways with relatively limited amounts of machining.

SUMMARY

The techniques of this disclosure generally relate to surgical implants having a body portion, and at least one of a first tier attached to an upper surface of the body portion, and a second tier attached to a lower surface of the body portion, where at least one of the first tier includes at least first channels communicating with channels formed in the upper surface, and the second tier includes at least second channels communicating with channels formed in the lower surface, the communication of these channels creating pathways to afford bone ingrowth into and therethrough to facilitate fusion of the surgical implant to bone.

In one aspect, the present disclosure provides a spinal implant for implantation into a disc space between adjacent vertebral bodies, the spinal implant including a body portion having a first end surface, a second end surface, a first lateral side surface, a second lateral side surface, an upper surface, a lower surface, a first central axis extending through the first end surface and the second end surface, and a second central axis extending through the first lateral side and the second lateral side, the upper surface including a plurality of first channels between the first lateral side and the second lateral side, and the lower surface including a plurality of second channels between the first lateral side and the second lateral side; a first tier attached to at least a portion of the upper surface of the body portion, the first tier including a first layer and a second layer attached to one another, the first layer including a plurality of first slats arranged in a first arrangement, and each of the plurality of first slats being spaced apart from one another to form third channels therebetween, the second layer including a plurality of second slats arranged in a second arrangement, and each of the plurality of second slats being spaced apart from one another to form fourth channels therebetween, the plurality of first slats and the plurality of second slats transversely intersecting one another to form first apertures affording communication between the third channels and the fourth channels, and a second tier attached to at least a portion of the lower surface of the body portion, the second tier including a third layer and a fourth layer attached to one another, the third layer including a plurality of third slats arranged in a third arrangement, and each of the plurality of third slats being spaced apart from one another to form fifth channels therebetween, the fourth layer including a plurality of fourth slats arranged in a fourth arrangement, and each of the plurality of fourth slats being spaced apart from one another to form sixth channels therebetween, the plurality of third slats and the plurality of fourth slats transversely intersecting one another to form second apertures affording communication between the fifth channels and the sixth channels, where the first layer of the first tier is attached to the upper surface of the body portion, the plurality of first slats intersecting the upper surface transversely to the first channels to form third apertures affording communication between the first channels and the third channels, and the third layer of the second tier is attached to the lower surface of the body portion, the plurality of third slats intersecting the lower surface transversely to the second channels to form fourth apertures affording communicating between the second channels and the fifth channels; and where at least a first pathway is formed from one of the fourth channels, through one of the first apertures, through one of the third channels, through one of the third apertures, and to one of the first channels, and at least a second pathway is formed from one of the sixth channels, through one of the second apertures, through one of the fifth channels, through one of the fourth apertures, to one of the second channels.

In another aspect, the disclosure provides a spinal implant for implantation into a disc space between adjacent vertebral bodies, the spinal implant including a body portion having a first end surface, a second end surface, a first lateral side surface, a second lateral side surface, an upper surface, a lower surface, a first central axis extending through the first end surface and the second end surface, and a second central axis extending through the first lateral side and the second lateral side, the upper surface including a plurality of first channels between the first lateral side and the second lateral side; and a first tier attached to at least a portion of the upper surface of the body portion, the first tier including a first layer and a second layer attached to one another, the first layer including a plurality of first slats arranged in a first arrangement, and each of the plurality of first slats being spaced apart from one another to form second channels therebetween, the second layer including a plurality of second slats arranged in a second arrangement, and each of the plurality of second slats being spaced apart from one another to form third channels therebetween, the plurality of first slats and the plurality of second slats transversely intersecting one another to form first apertures affording communication between the third channels and the fourth channels, where the first layer of the first tier is attached to the upper surface of the body portion, the plurality of first slats intersecting the upper surface transversely to the first channels to form second apertures affording communication between the first channels and the third channels; and where at least a first pathway is formed from one of the third channels, through one of the first apertures, through one of the second channels, through one of the second apertures, and to one of the first channels.

In yet another aspect, the disclosure provides a spinal implant for implantation into a disc space between adjacent vertebral bodies, the spinal implant including a body portion having a first end surface, a second end surface, an upper surface, a lower surface, and a first central axis extending through the first end surface and the second end surface, the upper surface including a plurality of first channels; and a first tier attached to at least a portion of the upper surface of the body portion, the first tier including a first layer and a second layer attached to one another, the first layer including a plurality of first slats arranged in a first arrangement one of aligned with and transverse to the first central axis, and each of the plurality of first slats being spaced apart from one another to form second channels therebetween, the second layer including a plurality of second slats arranged in a second arrangement, and each of the plurality of second slats being spaced apart from one another to form third channels therebetween, the plurality of first slats and the plurality of second slats transversely intersecting one another to form first apertures affording communication between the third channels and the fourth channels, where the first layer of the first tier is attached to the upper surface of the body portion, the plurality of first slats intersecting the upper surface transversely to the first channels to form second apertures affording communication between the first channels and the third channels.

The details of one or more aspects of the disclosure as set forth in the accompanying drawings and the description below. Other features, objects, and advantages of the techniques described in this disclosure will be apparent from the description and drawings, and from the claims.

BRIEF DESCRIPTION OF DRAWINGS

FIG. 5 is a bottom perspective view that illustrates a lower second tier attached to the body portion of the first embodiment of the spinal implant;

FIG. 6 is a top perspective view that illustrates the lower second tier of FIG. 5;

FIG. 9 is a top perspective view that illustrates a third tier of a second embodiment of a spinal implant;

FIG. 10 is a bottom perspective view that illustrates the third tier of FIG. 9;

DETAILED DESCRIPTION

Figure 1:
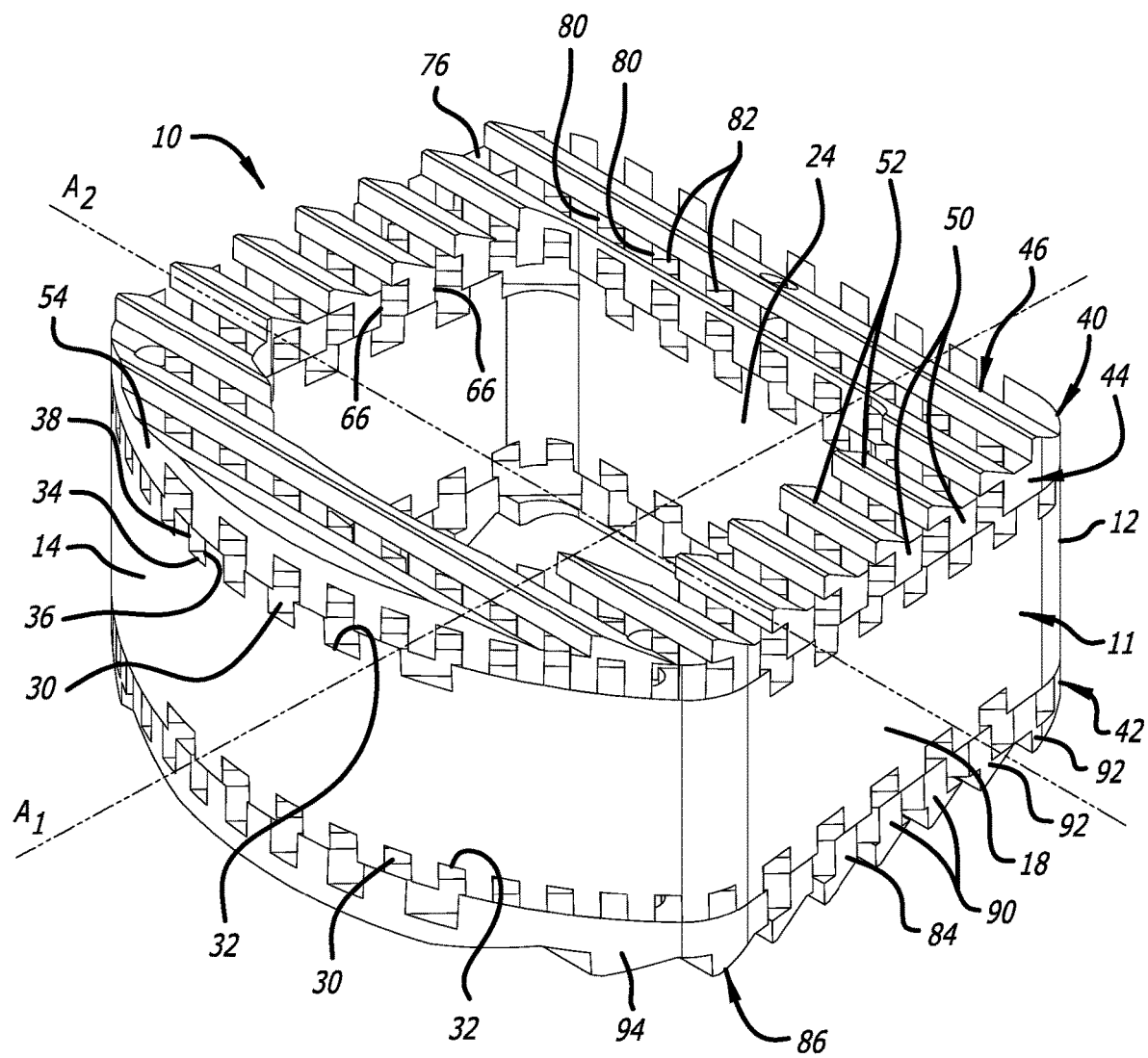
FIG. 1 is a top perspective view that illustrates a first embodiment of a spinal implant.

An implant according to a preferred embodiment of the present disclosure is generally indicated by the numeral 10 in FIGS. 1, 2, 7, and 8. As depicted in FIGS. 1, 2, 7, and 8, the implant 10 can be an interbody spinal fusion implant, but the present disclosure is not limited to such an application. Implants according to the present disclosure can be used throughout the body where there is a need for an implant having bone ingrowth properties and properties for resisting migration after implantation thereof.

The implant 10 is configured for insertion into a disc space between adjacent vertebral bodies. As discussed below, the implant includes one or more tiers stacked on one another. The various tiers of the implant 10 and the remainder of the implant 10 can be made of metals, polymers, ceramics, bioresorbable materials, non-bioresorbable materials, and/or organic/inorganic minerals found in bone. Furthermore, the multiple tiers can be joined together using chemical, mechanical, and/or physical processes including, but not limited to biocompatible adhesives, fasteners, brazing, welding (such as ultrasonic welding), and/or other bonding techniques, and when joined the multiple tiers define voids for facilitating bone ingrowth into and through the implant 10 and/or provide bone engagement surfaces resisting migration of the implant 10 after implantation.

The implant 10 includes a body portion 11 having a first end surface 12 and a second end surface 14, and a length between the first end surface 12 and the second end surface 14 along a first central axis $A_1$ extending through the first end surface 12 and the second end surface 14. Furthermore, the body portion 11 of the implant 10 includes a first lateral side surface 16 and a second lateral side surface 18, and a length between the first lateral side surface 16 and the second lateral side surface 18 along a second central axis $A_2$ extending through the first lateral side surface 16 and the second lateral side surface 18.

Figure 7:
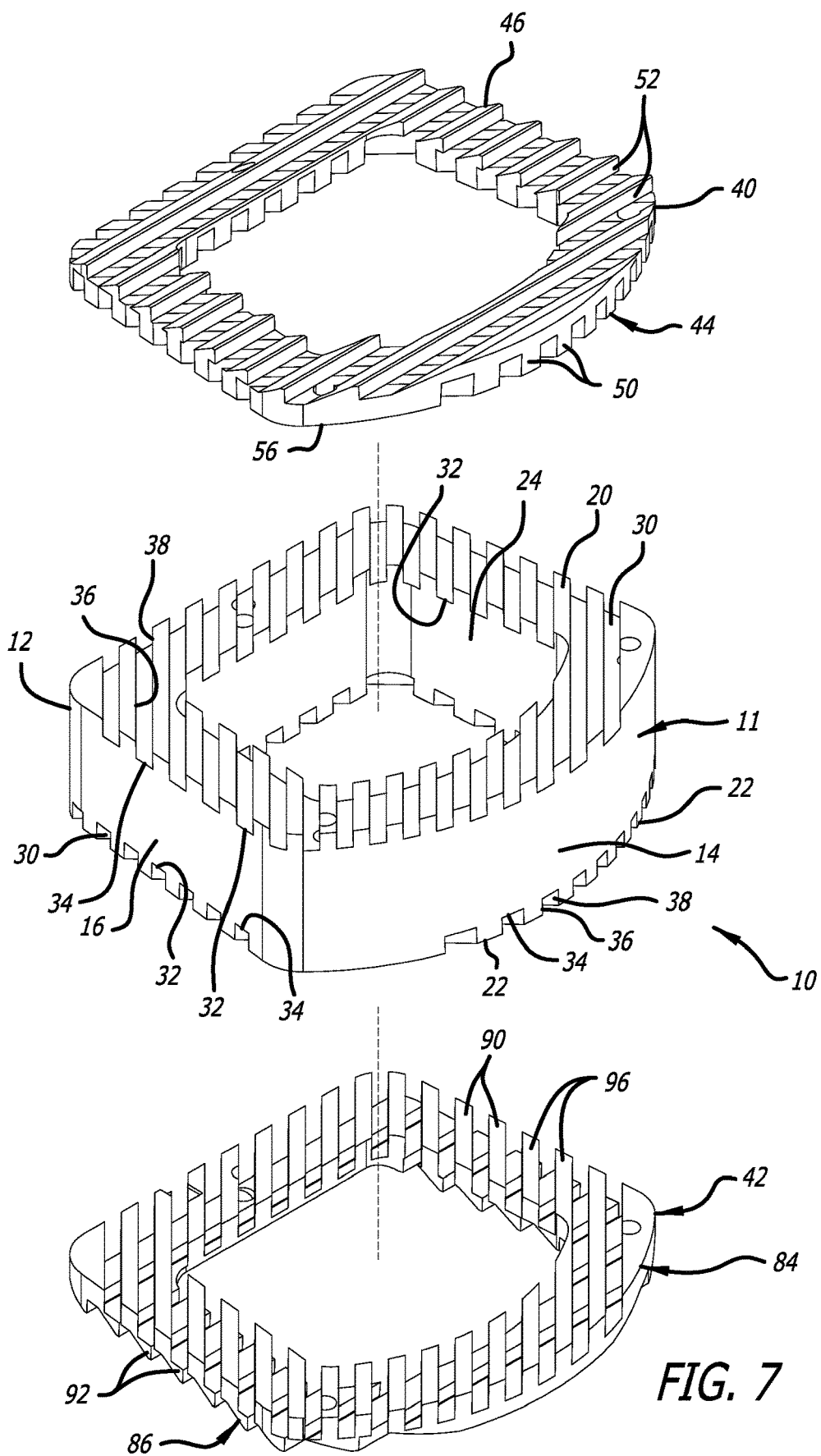
FIG. 7 is a top perspective exploded view that illustrates the first embodiment of the spinal implant.

Additionally, as depicted in FIG. 7, the body portion 11 of the implant 10 includes an upper surface 20 and a lower surface 22, and aperture 24 extending through the body portion 11 between the upper surface 20 and the lower surface 22. The aperture 24 can be sized to receive bone-growth promoting materials therein facilitating bone growth through the implant 10 between adjacent vertebral bodies.

The first end surface 12, the second end surface 14, the first lateral side surface 16, the second lateral side surface 18, the upper surface 20, and the lower surface 22 can include portions that are flattened and/or smoothly or sharply contoured with various convexities, concavities, and/or other surface structures or surface roughenings. Furthermore, the first end surface 12, the second end surface 14, the first lateral side surface 16, the second lateral side surface 18, the upper surface 20, and the lower surface 22 can be arranged at various angles with respect to one another. The flats, contours, surface structures, and/or angles of these surfaces can be configured to complimentarily interface with anatomical structures.

Figure 2:
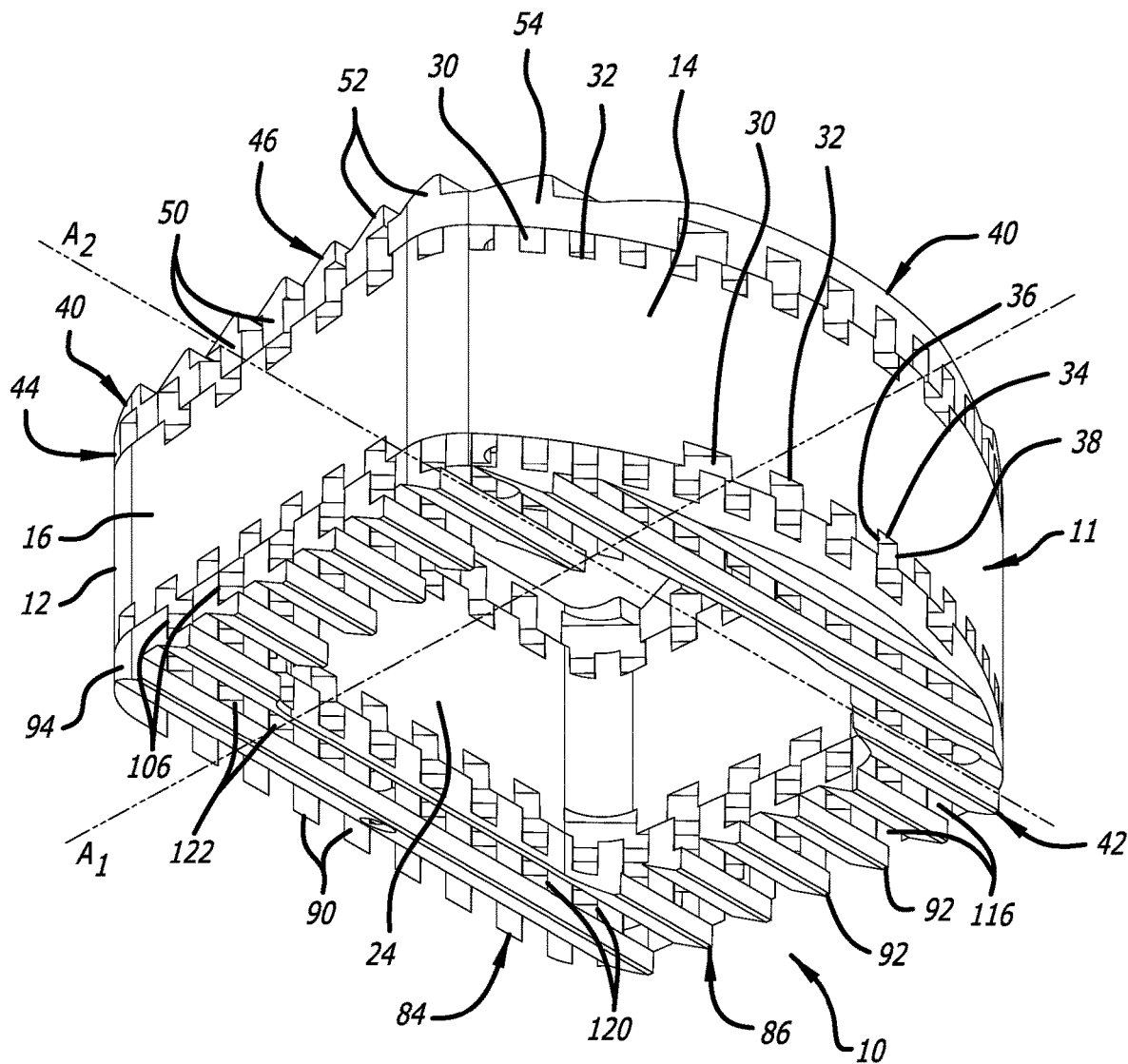
FIG. 2 is a bottom perspective view that illustrates the first embodiment of the spinal implant.

As depicted in FIGS. 1, 2, 7, and 9, for example, the first end surface 12, the first lateral side surface 16, and the second lateral side surface 18 have flattened surfaces; the second end surface 14 has a smoothly contoured convex surface; and the upper surface 20 and the lower surface 22 have various channels 30 formed therein. As depicted in FIGS. 1 and 2, for example, the channels 30 extend in directions transverse to the first axis $A_1$ and the second axis $A_2$. To illustrate, the channels 30 are arranged parallel to one another, and oriented to extend across the upper surface 20 and the lower surface 22 at a transverse angle with respect to the first axis $A_1$ and the second axis $A_2$. The channels 30 intersect the first end surface 12, the second end surface 14, the first lateral side surface 16, and the second lateral side surface 18, and/or the aperture 24 to form openings 32. However, the arrangement and the orientation of the channels 30 are not so limited. The channels 30 could extend parallel to the first axis $A_1$ and to one another across the upper surface 20 and the lower surface 22 between the first end surface 12 and the second end surface 14. The channels 30 also could extend parallel to the second axis $A_2$ and to one another across the upper surface 20 and the lower surface 22 between the first lateral side surface 16 and the second lateral side surface 18, and between portions of the second end surface 14 adjacent the first lateral side surface 16 and portions of the second end surface 14 adjacent the second lateral side surface 18. Furthermore, these various orientations and arrangements of channels 30 could be combined with one another and correspondingly cross one another at various angles.

Figure 8:
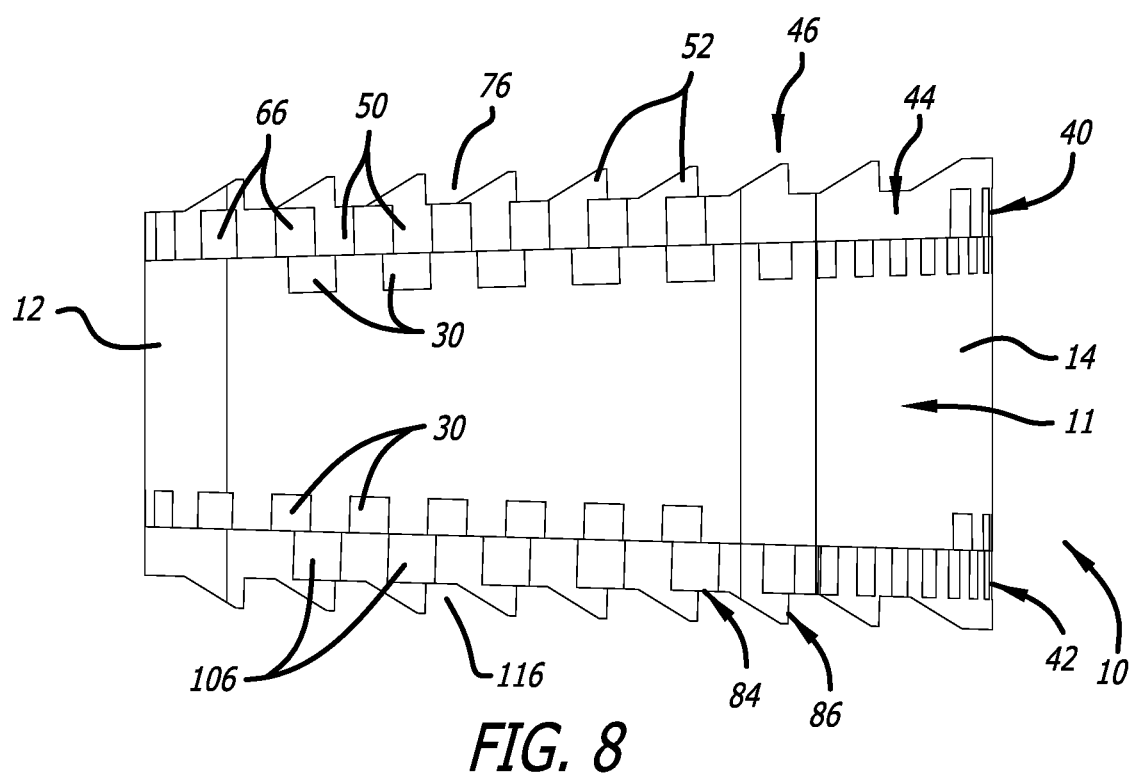
FIG. 8 is a side elevational view that illustrates the first embodiment of the spinal implant.

The channels 30 include a bottom surface 34, a first substantially-vertical surface 36, and a second substantially-vertical surface 38. As depicted in FIG. 8, the upper surface 20 and the lower surface 22 appear to be crenulated because of the channels 30 formed therein. While the first substantially-vertical surface 36 and the second substantially-vertical surface 38 are substantially perpendicular to the bottom surface 34, the bottom surface 34, the first substantially-vertical surface 36, and the second substantially-vertical surface 38 can be arranged at various angles with respect to one another. Furthermore, the bottom surface 34, the first substantially-vertical surface 36, and the second substantially-vertical surface 38 can have different sizes in planes perpendicular to the lengths of the channels 30. Additionally, while the portions of the upper surface 20 and the lower surface 22 between the channels 30 are substantially uniform in size, the portions of the upper surface 20 reside in the same plane and the portions of the lower surface 22 reside in the same plane, these portions of the upper surface 20 and the lower surface 22 could have various sizes and could be angled with respect to one another, and if another tier is not stacked thereon, these angled portions of the upper surface 20 and the lower surface 22 could serve as bone engagement surfaces for resisting migration of the implant 10.

The channels 30, when the tiers of the implant 10 are stacked on the body portion 11, together with the tiers provide voids for bone ingrowth. As depicted in FIGS. 1, 2, 7, and 8, the implant 10 includes a first tier 40 and a second tier 42 stacked on the upper surface 20 and the lower surface 22, respectively, of the body portion 11. The first tier 40 and the second tier 42 can be attached to the upper surface 20 and the lower surface 22, respectively, using the above-discussed chemical, mechanical, and/or physical processes.

The first tier 40 includes at least two layers, a first layer 44 and a second layer 46. The first layer 44 and the second layer 46 can be unitarily formed with one another, or attached to one another using chemical, mechanical, and/or physical processes. For example, the first layer 44 and the second layer 46 can be attached to one another using the above-discussed chemical, mechanical, and/or physical processes.

Figures 3, 4:
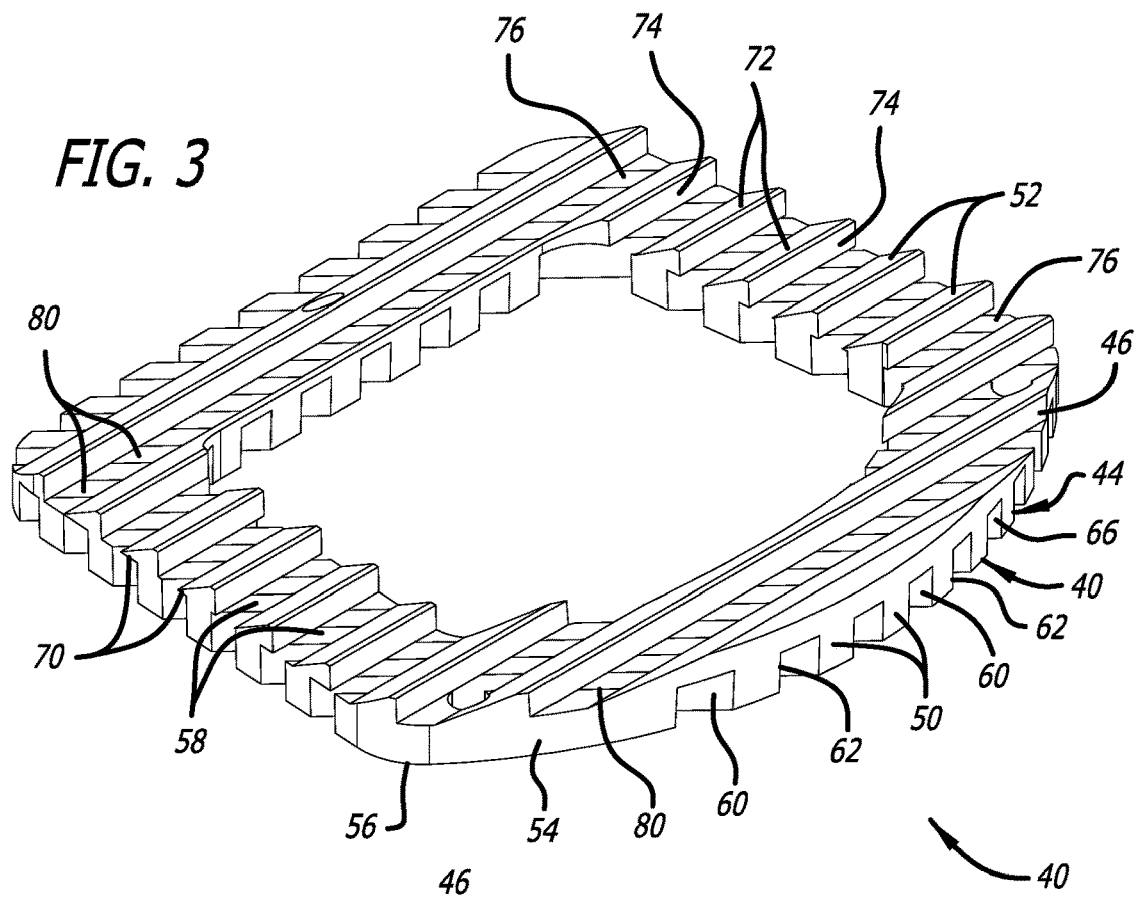
FIG. 3 is a top perspective view that illustrates an upper first tier attached to a body portion of the first embodiment of the spinal implant.
FIG. 4 is a bottom perspective view that illustrates the upper first tier of FIG. 3.

As depicted in FIGS. 3 and 4, the first layer 44 is provided on the bottom of the first tier 40 and is formed by a plurality of first slats (or ribs) 50 arranged in parallel to one another, and the second layer 46 is provided on the top of the first tier 40 and is formed by a plurality of second slats (or ribs) 52 arranged in parallel to one another. The first tier 40 includes a perimeter 54 between which the first slats 50 and the second slats 52 extend, and the perimeter 54 can at least generally match the outer dimensions of the upper surface 20. The first slats 50 and the second slats 52 include varying lengths between the perimeter 54 along mid-longitudinal axes of these slats.

The first slats 50 each have a lower surface 56 and an upper surface 58, a first side surface 60, and a second side surface 62, and have rectangular cross-sections in planes perpendicular to the lengths thereof, and various channels 66 are formed between the first slats 50. Furthermore, the second slats 52 each have a lower surface 70, an upper surface 72, and a side surface 74, and have triangular cross-sections in planes perpendicular to the lengths thereof where the upper surface 72 and the side surface 74 are oriented at an acute angle with respect to one another and intersect at a point, and various channels 76 are formed between the second slats 52. The points formed by the intersections of the upper surfaces 72 and the side surfaces 74 serve to engage bone to resist migration of the spinal implant 10 after implantation thereof in the disc space, and the intersection of the first slats 50 and the second slats 52 create openings 80 that afford communication between the channels 66 and 76.

However, these cross-sections of the first slats 50 and the second slats 52 are not so limited, and can have a variety of shapes for the cross-sections thereof. Furthermore, while, as depicted in FIGS. 3 and 4, the sizes of the cross-sections of a substantial majority the first slats 50 are substantially uniform, and the sizes of the cross-sections of a substantial majority of the second slats 52 are substantially uniform, the sizes of the cross-sections of the first slats 50 and the second slats 52 could have various sizes. And, while, as depicted in FIGS. 3 and 4, the sizes of the channels 66 between the first slats 50 are substantially uniform in cross-sections perpendicular to the lengths thereof and the sizes of the channels 76 between the second slats 52 are substantially uniform in cross-sections perpendicular to the lengths thereof, the sizes of these channels 66 and 76 could be varied. Additionally, the lower surfaces 56 can reside in the same plane to facilitate attachment to the upper surface 20 of the body portion 11, the upper surfaces 58 can reside in the same plane to facilitate attachment to the second layer 46, the lower surfaces 70 can reside in the same plane to facilitate attachment to the first layer 44, and, as discussed below, the upper surfaces 72 can afford insertion, and the upper surfaces 72 and the side surfaces 74 can resist migration of the implant 10.

When the first tier 40 is attached to the upper surface 20 of the body portion 11, the first slats 50 are oriented at a transverse angle with respect to the first axis $A_1$ and the second axis $A_2$, and the second slats 52 extend parallelly to the second axis $A_2$. The orientation of the second slats 52 allow the upper surfaces 72 to afford insertion, and the upper surfaces 72 and the side surfaces 74 to resist migration of the implant 10. However, the arrangement and the orientation of the first slats 50 and the second slats 52 are not so limited. To illustrate, the first slats 50 could extend in parallel to the first axis $A_1$, and the second slats 52 could extend in parallel to the second axis $A_2$, or vice versa. Furthermore, the first slats 50 and the second slats 52 can be oriented at different transverse angles with respect to the first axis $A_1$ and the second axis $A_2$.

After the attachment of the first tier 40 to the upper surface 20, openings 82 are created by the intersection of the first slats 50 and the upper surface 20. The openings 80 afford communication between the channels 66 and 76, and the openings 82 afford communication between the channels 30 and 66. As such, non-linear pathways can be formed through the openings 32 and the channels 30 of the upper surface 20, the openings 82, the channels 66, the openings 80, and the channels 76. The voids formed by these pathways afford bone ingrowth into and therethrough to facilitate fusion of the implant 10 to an upper one of the adjacent vertebral bodies when the implant 10 is positioned in the disc space.

The second tier 42 includes at least two layers, a first layer 84 and a second layer 86. The first layer 84 and the second layer 86 can be unitarily formed with one another, or attached to one another using chemical, mechanical, and/or physical processes. For example, the first layer 84 and the second layer 86 can be attached to one another using the above-discussed chemical, mechanical, and/or physical processes.

As depicted in FIGS. 5 and 6, the first layer 84 is provided on the top of the second tier 42 and is formed by a plurality of first slats (or ribs) 90 arranged in parallel to one another, and the second layer 86 is provided on the bottom of the second tier 42 and is formed by a plurality of second slats (or ribs) 92 arranged in parallel to one another. The second tier 42 includes a perimeter 94 between which the first slats 90 and the second slats 92 extend, and the perimeter 94 can at least generally match the outer dimensions of the upper surface 20. The first slats 90 and the second slats 92 include varying lengths between the perimeter 94 along mid-longitudinal axes of these slats.

The first slats 90 each have an upper surface 96 and a lower surface 98, a first side surface 100, and a second side surface 102, and have rectangular cross-sections in planes perpendicular to the lengths thereof, and various channels 106 are formed between the first slats 90. Furthermore, the second slats 92 each have an upper surface 110, a lower surface 112, and a side surface 114, and have triangular cross-sections in planes perpendicular to the lengths thereof where the lower surface 112 and the side surface 114 are oriented at an acute angle with respect to one another, and various channels 116 are formed between the second slats 92. The points formed by the intersections of the lower surfaces 112 and the side surfaces 114 serve to engage bone to resist migration of the spinal implant 10 after implantation thereof in the disc space, and the intersection of the first slats 90 and the second slats 92 create openings 120 that afford communication between the channels 106 and 116.

However, these cross-sections of the first slats 90 and the second slats 92 are not so limited, and can have a variety of shapes for the cross-sections thereof. Furthermore, while, as depicted in FIGS. 5 and 6, the sizes of the cross-sections of a substantial majority of the first slats 90 are substantially uniform, and the sizes of the cross-sections of a substantial majority of the second slats 92 are substantially uniform, the sizes of the cross-sections of the first slats 90 and the second slats 92 could have various sizes. And, while, as depicted in FIGS. 5 and 6, the sizes of the channels 106 between the first slats 90 are substantially uniform in cross-section perpendicular to the lengths thereof and the sizes of the channels 116 between the second slats 92 are substantially uniform in cross-section perpendicular to the lengths thereof, the sizes of these channels 106 and 116 could be varied. Additionally, the upper surfaces 96 can reside in the same plane to facilitate attachment to the lower surface 22 of the body portion 11, the lower surfaces 98 can reside in the same plane to facilitate attachment to the second layer 86, the upper surfaces 110 can reside in the same plane to facilitate attachment to the first layer 44, and, as discussed below, the lower surfaces 112 can afford insertion, and the lower surfaces 112 and the side surfaces 114 can resist migration of the implant 10.

When the first tier 42 is attached to the lower surface 22 of the body portion 11, the first slats 90 are oriented at a transverse angle with respect to the first axis $A_1$ and the second axis $A_2$, and the second slats 92 extend parallelly to the second axis $A_2$. The orientation of the second slats 92 allow the lower surfaces 112 to afford insertion, and the lower surfaces 112 and the side surfaces 114 to resist migration of the implant 10. However, the arrangement and the orientation of the first slats 90 and the second slats 92 are not so limited. To illustrate, the first slats 90 could extend in parallel to the first axis $A_1$, and the second slats 92 could extend in parallel to the second axis $A_2$, or vice versa. Furthermore, the first slats 90 and the second slats 92 can be oriented a different transverse angles with respect to the first axis $A_1$ and the second axis $A_2$.

After the attachment of the second tier 42 to the lower surface 22, openings 122 are created by the intersection of the first slats 50 and the lower surface 22. The openings 120 afford communication between the channels 106 and 116, and the openings 122 afford communication between the channels 30 and 106. As such, non-linear pathways can be formed through the openings 32 and the channels 30 in the lower surface 22, the openings 122, the channels 106, the openings 120, and the channels 116. The voids formed by these pathways afford bone ingrowth into and therethrough to facilitate fusion of the implant 10 to a lower one of the adjacent vertebral bodies when the implant 10 is positioned in the disc space.

As such, after insertion of the implant 10 into the disc space, bone ingrowth through the voids formed by the above-discussed pathways serves in fusing the upper vertebral body and the lower vertebral body to one another through the implant 10. The voids formed by these above-discussed pathways can receive bone ingrowth and can be filled with bone-growth promoting substances to promote such bone ingrowth.

Figure 11:
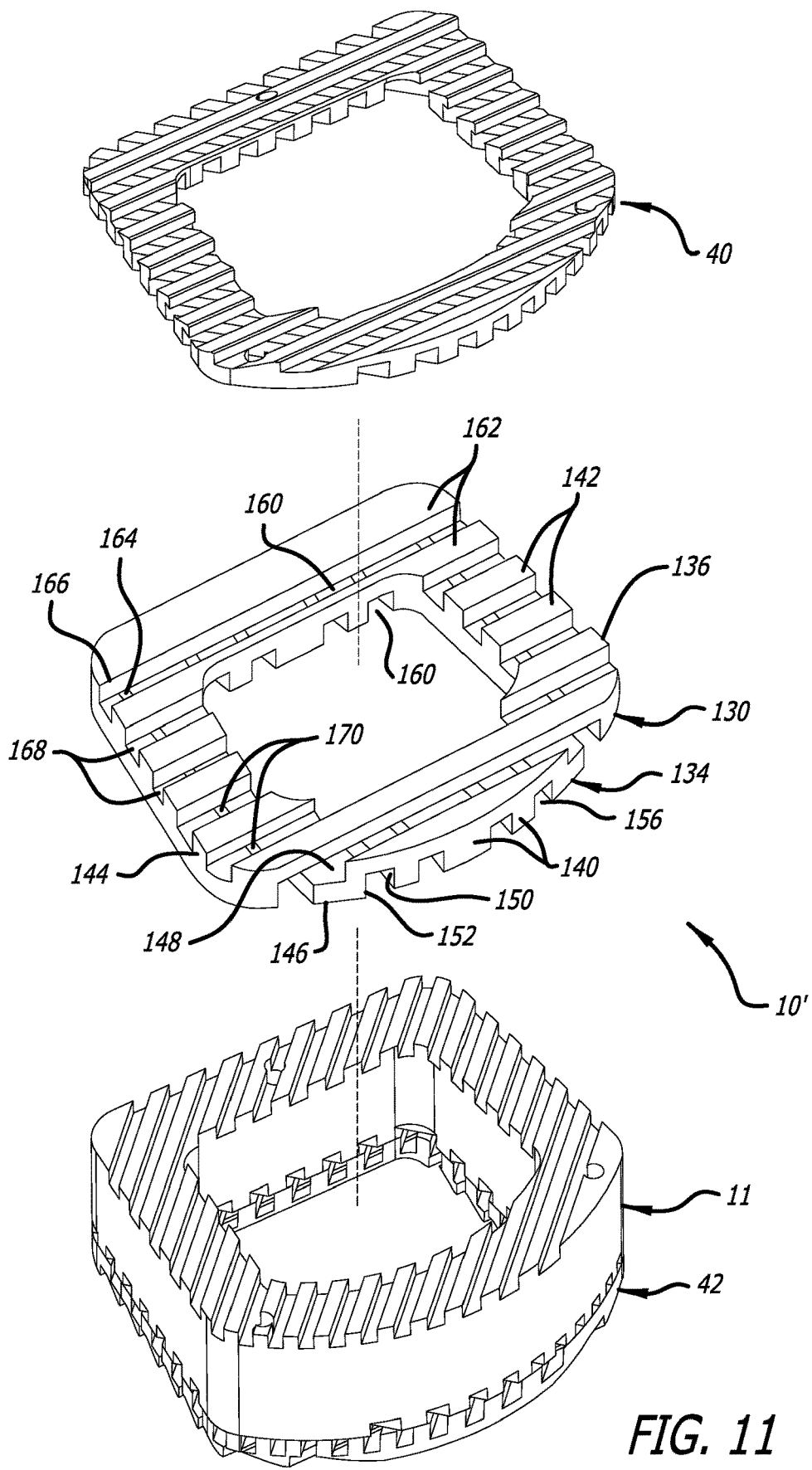
FIG. 11 is a top perspective partially exploded view that illustrates the second embodiment of the spinal implant.
Figure 12:
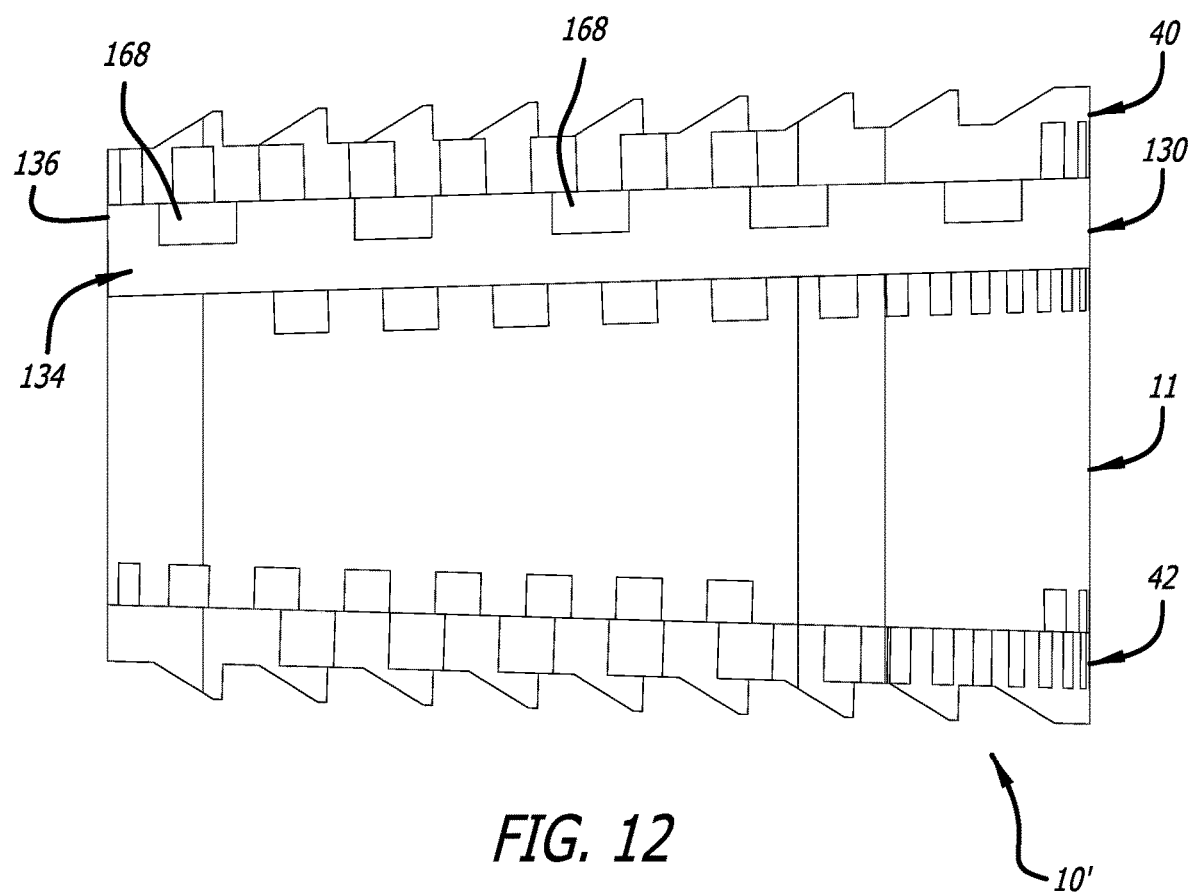
FIG. 12 is a side elevational view of the second embodiment that illustrates the spinal implant.

Additionally, additional tiers can be stacked on the first tier 40 and/or the second tier 42, and/or positioned between the first tier 40 and the body portion 11 and/or between the second tier 42 and the body portion 11. For example, as depicted in FIGS. 11 and 12, a third tier 130 can be provided between the body portion 11 and the first tier 40 to form an implant 10'. As discussed below, the additional tiers (such as the third tier 130, and similar to the first tier 40 and the second tier 42) provide for additional pathways and voids formed thereby to receive bone ingrowth.

The third tier 130 includes at least two layers, a first layer 134 and a second layer 136. The first layer 134 and the second layer 136 can be unitarily formed with one another, or attached to one another using chemical, mechanical, and/or physical processes. For example, the first layer 134 and the second layer 136 can be attached to one another using the above-discussed chemical, mechanical, and/or physical processes.

As depicted in FIGS. 9 and 10, the first layer 134 is provided on the bottom of the third tier 130 and is formed by a plurality of first slats (or ribs) 140 arranged in parallel to one another, and the second layer 136 is provided on the top of the third tier 130 and is formed by a plurality of second slats (or ribs) 142 arranged in parallel to one another. The third tier 130 includes a perimeter 144 between which the first slats 140 and the second slats 142 extend, and the perimeter 144 can at least generally match the outer dimensions of the upper surface 20 of the body portion 11 and the lower surface 98 of the first slats 50 of the first tier 40. The first slats 140 and the second slats 142 include varying lengths between the perimeter 144 along mid-longitudinal axes of these slats.

The first slats 140 each have a lower surface 146 and an upper surface 148, a first side surface 150, and a second side surface 152, and have rectangular cross-sections in planes perpendicular to the lengths thereof, and various channels 156 are formed between the first slats 140. Furthermore, the second slats 142 each have a lower surface 160, an upper surface 162, a first side surface 164, and a second side surface 166, and also have rectangular cross-sections in planes perpendicular to the lengths thereof, and various channels 168 are formed between the second slats 142. The intersection of the first slats 140 and the second slats 142 create openings 170 that afford communication between the channels 156 and 168.

However, these cross-sections of the first slats 140 and the second slats 142 are not so limited, and can have a variety of shapes for the cross-sections thereof. Furthermore, while, as depicted in FIGS. 9 and 10, the sizes of the cross-sections of a substantial majority the first slats 140 are substantially uniform, and the sizes of the cross-sections of a substantial majority of the second slats 142 are substantially uniform, the sizes of the cross-sections of the first slats 140 and the second slats 142 could have various sizes. And, while, as depicted in FIGS. 9 and 10, the sizes of the channels 156 between the first slats 140 are substantially uniform in cross-sections perpendicular to the lengths thereof and the sizes of the channels 168 between the second slats 142 are substantially uniform in cross-sections perpendicular to the lengths thereof, the sizes of these channels 156 and 168 could be varied. Additionally, the lower surfaces 146 can reside in the same plane to facilitate attachment to the upper surface 20 of the body portion 11, and the upper surfaces 148 can reside in the same plane to facilitate attachment to the lower surface 98 of the first slats 50 of the first tier 40.

When the third tier 130 is attached to the upper surface 20 of the body portion 11, the first slats 140 extend parallelly to the first axis $A_1$, and the second slats 142 extend parallelly to the second axis $A_2$. However, the arrangement and the orientation of the first slats 140 and the second slats 142 are not so limited. To illustrate, the first slats 140 could extend in parallel to the second axis $A_2$, and the second slats 142 could extend in parallel to the first axis $A_1$. Furthermore, the first slats 140 and the second slats 142 can be oriented at different transverse angles with respect to the first axis $A_1$ and the second axis $A_2$.

After the attachment of the third tier 130 to the upper surface 20 of the body portion 11 and the attachment of the first tier 40 to the third tier 130, openings (not shown) are created by the intersection of the first slats 140 of the third tier 130 and the upper surface 20, and openings (not shown) are created by the intersection of the first slats 50 of the first tier 40 and the second slats 142 of the third tier 130. The openings 80 afford communication between the channels 66 and 76, the openings created by the intersection of the first slats 50 and the second slats 142 afford communication between the channels 66 and 168, the openings 170 created by the intersection of the first slats 140 and the second slats 142 afford communication between the channels 156 and 168, and the openings created by the intersection of the first slats 140 and the upper surface 20 affords communication between the channels 30 and 156. As such, non-linear pathways can be formed through these openings and these channels, and the voids formed by these pathways afford bone ingrowth into and therethrough to facilitate fusion of the implant 10' to an upper one of the adjacent vertebral bodies when the implant 10' is positioned in the disc space. Bone ingrowth with respect second tier 42 of the implant 10' can occur in similar fashion as described above.

It should be understood that various aspects disclosed herein may be combined in different combinations than the combinations specifically presented in the description and the accompanying drawings. It should also be understood that, depending on the example, certain acts or events of any of the processes of methods described herein may be performed in a different sequence, may be added, merged, or left out altogether (e.g., all described acts or events may not be necessary to carry out the techniques). In addition, while certain aspect of this disclosure are described as being performed by a single module or unit for purposes of clarity, it should be understood that the techniques of this disclosure may be performed by a combination of units or modules associated with, for example, a medical device.

We claim:

1. A spinal implant for implantation into a disc space between adjacent vertebral bodies, the spinal implant comprising:
   a first end, an opposite second end, a first lateral side between the first end and the second end, and a second lateral side between the first end and the second end;
   a body portion having a first end surface at the first end, a second end surface at the second end, a first lateral side surface at the first lateral side, a second lateral side surface at the second lateral side, an upper surface, a lower surface, a first central axis extending through the first end surface and the second end surface, and a second central axis extending through the first lateral side and the second lateral side, the upper surface including a plurality of first channels between the first lateral side and the second lateral side, and the lower surface including a plurality of second channels between the first lateral side and the second lateral side;
   a first tier attached to at least a portion of the upper surface of the body portion, the first tier including a first layer and a second layer attached to one another,
   the first layer including a plurality of first slats arranged in a first arrangement, and adjacent ones of the plurality of first slats being spaced apart from one another to form third channels therebetween, each of the first slats having a mid-longitudinal axis, and each of the third channels having a mid-longitudinal axis, the mid-longitudinal axes of the first slats and the mid-longitudinal axes of the third channels being substantially aligned with one another, at least two of the first slats extending from adjacent one of the first lateral side and the second lateral side to adjacent one of the first end and the second end, the at least two of the first slats being oriented in first transverse angles with respect to the first central axis and the second central axis,
   the second layer including a plurality of second slats arranged in a second arrangement, and adjacent ones of the plurality of second slats being spaced apart from one another to form fourth channels therebetween, each of the second slats having a mid-longitudinal axis, and each of the fourth channels having a mid-longitudinal axis, the mid-longitudinal axes of the second slats and the mid-longitudinal axes of the fourth channels being substantially aligned with one another, at least two of the second slats extending from adjacent the first lateral side to adjacent the second lateral side, the plurality of first slats and the plurality of second slats transversely intersecting one another to form first apertures affording communication between the third channels and the fourth channels, and a second tier attached to at least a portion of the lower surface of the body portion, the second tier including a third layer and a fourth layer attached to one another, the third layer including a plurality of third slats arranged in a third arrangement, and adjacent ones of the plurality of third slats being spaced apart from one another to form fifth channels therebetween, each of the third slats having a mid-longitudinal axis, and each of the fifth channels having a mid-longitudinal axis, the mid longitudinal axes of the thirst slats and the mid-longitudinal axes of the fifth channels being substantially aligned with one another, at least two of the third slats extending from adjacent one of the first lateral side and the second lateral side to adjacent one of the first end and the second end, the fourth layer including a plurality of fourth slats arranged in a fourth arrangement, and adjacent ones of the plurality of fourth slats being spaced apart from one another to form sixth channels therebetween, each of fourth slats having a mid-longitudinal axis, and each of the sixth channels having a mid-longitudinal axis, the mid-longitudinal axes of the fourth slats and mid-longitudinal axes of the sixth channels being substantially aligned with one another, at least two of the fourth slats extending from adjacent the first lateral side to adjacent the second lateral side, the plurality of third slats and the plurality of fourth slats transversely intersecting one another to form second apertures affording communication between the fifth channels and the sixth channels, wherein the first layer of the first tier is attached to the upper surface of the body portion, the plurality of first slats intersecting the upper surface transversely to the first channels to form third apertures affording communication between the first channels and the third channels, and the third layer of the second tier is attached to the lower surface of the body portion, the plurality of third slats intersecting the lower surface transversely to the second channels to form fourth apertures affording communicating between the second channels and the fifth channels; and wherein at least a first pathway is formed from one of the fourth channels, through one of the first apertures, through one of the third channels, through one of the third apertures, and to one of the first channels, and at least a second pathway is formed from one of the sixth channels, through one of the second apertures, through one of the fifth channels, through one of the fourth apertures, to one of the second channels.

2. The spinal implant of claim 1, wherein in the second arrangement, the plurality of second slats are oriented in substantial alignment with the second central axis.

3. The spinal implant of claim 2, wherein in the third arrangement, the plurality of third slats are oriented in second transverse angles with respect to the first central axis and the second central axis.

4. The spinal implant of claim 3, wherein in the fourth arrangement, the plurality of fourth slats are oriented in substantial alignment with the second central axes.

5. The spinal implant of claim 1, wherein the plurality of first slats includes a first slat and a second slat, each of the first slat and the second slat including a length and a cross-section perpendicular to the length, the cross-sections of the first slat and the second slat each including a lower surface, and the lower surfaces of the first slat and the second slat residing in a first plane to facilitate attachment to the upper surface of the body portion.

6. The spinal implant of claim 1, wherein the plurality of second slats includes a first slat and a second slat, each of the first slat and the second slat including a length and a cross-section perpendicular to the length, the cross-sections of the first slat and the second slat each including an upper surface and a side surface oriented at an acute angle with respect to one another to create a point for resisting migration after implantation of the spinal implant in the disc space.

7. The spinal implant claim 1, further comprising a third tier attached to the first tier, the third tier including a first layer including a plurality of fifth slats and a second layer including a plurality of sixth slats.

8. A spinal implant for implantation into a disc space between adjacent vertebral bodies, the spinal implant comprising:

a first end, an opposite second end, a first lateral side between the first end and the second end, and a second lateral side between the first end and the second end;

a body portion having a first end surface at the first end, a second end surface at the second end, a first lateral side surface at the first lateral side, a second lateral side surface at the second lateral side, an upper surface, a lower surface, a first central axis extending through the first end surface and the second end surface, and a second central axis extending through the first lateral side and the second lateral side, the upper surface including a plurality of first channels between the first lateral side and the second lateral side; and a first tier attached to at least a portion of the upper surface of the body portion, the first tier including a first layer and a second layer attached to one another, the first layer including a plurality of first slats arranged in a first arrangement, and adjacent ones of the plurality of first slats being spaced apart from one another to form second channels therebetween, each of the first slats having a mid-longitudinal axis, and each of the second channels having a mid-longitudinal axis, the mid-longitudinal axes of the first slats and the mid-longitudinal axes of the second channels being substantially aligned with one another, at least two of the first slats extending from adjacent one of the first lateral side and the second lateral side to adjacent one of the first end and the second end, the at least two of the first slats being oriented in first transverse angles with respect to the first central axis and the second central axis, the second layer including a plurality of second slats arranged in a second arrangement, and adjacent ones of the plurality of second slats being spaced apart from one another to form third channels therebetween, each of the second slats having a mid-longitudinal axis, and each of the third channels having a mid-longitudinal axis, the mid-longitudinal axes of the second slats and the mid-longitudinal axes of the third channels being substantially aligned with one another, at least two of the second slats extending from adjacent the first lateral side to adjacent the second lateral side, the plurality of first slats and the plurality of second slats transversely intersecting one another to form first apertures affording communication between the second channels and the third channels, wherein the first layer of the first tier is attached to the upper surface of the body portion, the plurality of first slats intersecting the upper surface transversely to the first channels to form second apertures affording communication between the first channels and the second channels; and wherein at least a first pathway is formed from one of the third channels, through one of the first apertures, through one of the second channels, through one of the second apertures, and to one of the first channels.

9. The spinal implant of claim 8, wherein in the second arrangement, the plurality of second slats are oriented in substantial alignment with the second central axis.

10. The spinal implant of claim 8, wherein the plurality of first slats includes a first slat and a second slat, each of the first slat and the second slat including a length and a cross-section perpendicular to the length, the cross-sections of the first slat and the second slat each including a lower surface, and the lower surfaces of the first slat and the second slat residing in a first plane to facilitate attachment to the upper surface of the body portion.

11. The spinal implant of claim 10, wherein the cross-sections of the first slat and the second slat are substantially rectangular.

12. The spinal implant of claim 8, wherein the plurality of second slats includes a first slat and a second slat, each of the first slat and the second slat including a length and a cross-section perpendicular to the length, the cross-sections of the first slat and the second slat each including an upper surface and a side surface oriented at an acute angle with respect to one another to create a point for resisting migration after implantation of the spinal implant in the disc space.

13. The spinal implant of claim 12, wherein the cross-sections of the first slat and the second slat are substantially triangular.

14. A spinal implant for implantation into a disc space between adjacent vertebral bodies, the spinal implant comprising:

a first end, an opposite second end, a first lateral side between the first end and the second end, and a second lateral side between the first end and the second end;

a body portion having a first end surface at the first end, a second end surface at the second end, a first lateral side surface at the first lateral side, a second lateral side surface at the second lateral side, an upper surface, a lower surface, and a first central axis extending through the first end surface and the second end surface, and a second central axis extending through the first lateral side and the second lateral side, the upper surface including a plurality of first channels; and a first tier attached to at least a portion of the upper surface of the body portion, the first tier including a first layer and a second layer attached to one another, the first layer including a plurality of first slats arranged in a first arrangement transverse to the first central axis, and adjacent ones of the plurality of first slats being spaced apart from one another to form second channels therebetween, each of the first slats having a mid-longitudinal axis, and each of the second channels having a mid-longitudinal axis, the mid-longitudinal axes of the first slats and the mid-longitudinal axes of the second channels being substantially aligned with one another, and the at least two of the first slats extending from adjacent one of the first lateral side and the second lateral side to adjacent one of the first end and the second end when the first arrangement is transverse to the first central axis and the second central axis, the second layer including a plurality of second slats arranged in a second arrangement, and adjacent one of the plurality of second slats being spaced apart from one another to form third channels therebetween, each of the second slats having a mid-longitudinal axis, and each of the third channels having a mid-longitudinal axis, the mid-longitudinal axes of the second slats and the mid-longitudinal axes of the third channels being substantially aligned with one another, the plurality of first slats and the plurality of second slats transversely intersecting one another to form first apertures affording communication between the second channels and the third channels, wherein the first layer of the first tier is attached to the upper surface of the body portion, the plurality of first slats intersecting the upper surface transversely to the first channels to form second apertures affording communication between the first channels and the second channels.

15. The spinal implant of claim 14, wherein the plurality of first slats includes a first slat and a second slat, each of the first slat and the second slat including a length and a cross-section perpendicular to the length, the cross-sections of the first slat and the second slat each including a lower surface, and the lower surfaces of the first slat and the second slat residing in a first plane to facilitate attachment to the upper surface of the body portion.

16. The spinal implant of claim 14, wherein the plurality of second slats includes a first slat and a second slat, each of the first slat and the second slat including a length and a cross-section perpendicular to the length, the cross-sections of the first slat and the second slat each including an upper surface and a side surface oriented at an acute angle with respect to one another to create a point for resisting migration after implantation of the spinal implant in the disc space.

17. The spinal implant of claim 15, wherein the cross-sections of the first slat and the second slat are substantially rectangular.

18. The spinal implant of claim 16, wherein the cross-sections of the first slat and the second slat are substantially triangular.

* * * * *